(12) United States Patent
Abe et al.

(10) Patent No.: US 8,042,378 B2
(45) Date of Patent: Oct. 25, 2011

(54) GAS AMOUNT MEASUREMENT DEVICE

(75) Inventors: Tetsuya Abe, Naka-gun (JP); Toshihisa Hatano, Naka-gun (JP); Hajime Hiratsuka, Naka-gun (JP); Koichi Hasegawa, Naka-gun (JP); Yasuhide Tajima, Naka-gun (JP); Soichiro Omachi, Tokyo (JP)

(73) Assignees: Japan Atomic Energy Agency, Ibaraki (JP); Nikkin Flux Inc., Tokyo (JP)

( * ) Notice: Subject to any disclaimer, the term of this patent is extended or adjusted under 35 U.S.C. 154(b) by 569 days.

(21) Appl. No.: 12/252,940

(22) Filed: Oct. 16, 2008

(65) Prior Publication Data

US 2009/0178460 A1    Jul. 16, 2009

(30) Foreign Application Priority Data

Jan. 15, 2008    (JP) .................................. 2008-006205

(51) Int. Cl.
G01N 33/20    (2006.01)
(52) U.S. Cl. .................................................. 73/19.07
(58) Field of Classification Search ................. 73/19.05, 73/19.07
See application file for complete search history.

(56) References Cited

U.S. PATENT DOCUMENTS

| | | | | |
|---|---|---|---|---|
| 2,729,969 A | * | 1/1956 | Innes | 73/38 |
| 3,517,543 A | * | 6/1970 | Gasser | 73/19.05 |
| 3,520,171 A | * | 7/1970 | Vantini et al. | 73/19.02 |
| 3,557,604 A | * | 1/1971 | Baeklund | 73/19.05 |
| 3,820,380 A | * | 6/1974 | Miller et al. | 436/75 |
| 3,949,590 A | * | 4/1976 | Boillot | 73/19.07 |
| 4,239,532 A | * | 12/1980 | Allersma et al. | 73/863.23 |
| 4,305,906 A | * | 12/1981 | Mikasa et al. | 422/62 |
| 4,345,467 A | * | 8/1982 | Carlson | 73/309 |

FOREIGN PATENT DOCUMENTS

| | | | |
|---|---|---|---|
| JP | 05133852 A | * | 5/1993 |
| JP | 2003-83865 | | 3/2003 |

* cited by examiner

*Primary Examiner* — John Fitzgerald
(74) *Attorney, Agent, or Firm* — Michael Best & Friedrich LLP

(57) ABSTRACT

A gas amount measuring device including a vacuum container, a first pipe, an air release valve being attached to the first pipe, a second pipe, a calibration gas generator being attached to the first pipe, a third pipe, a vacuum gauge, a first valve, a leak valve, a second valve, a turbomolecular pump, a third valve, and a roughing pump being attached to the third pipe in order from a vacuum container side, a first bypass pipe connecting the third pipe between the vacuum container and the first valve to the third pipe between the leak valve and the second valve, a fourth valve being attached to the first bypass pipe, and a second bypass pipe connecting the third pipe between the leak valve and the second valve to the third pipe between the third valve and the roughing pump, a fifth valve being attached to the second bypass pipe.

5 Claims, 4 Drawing Sheets

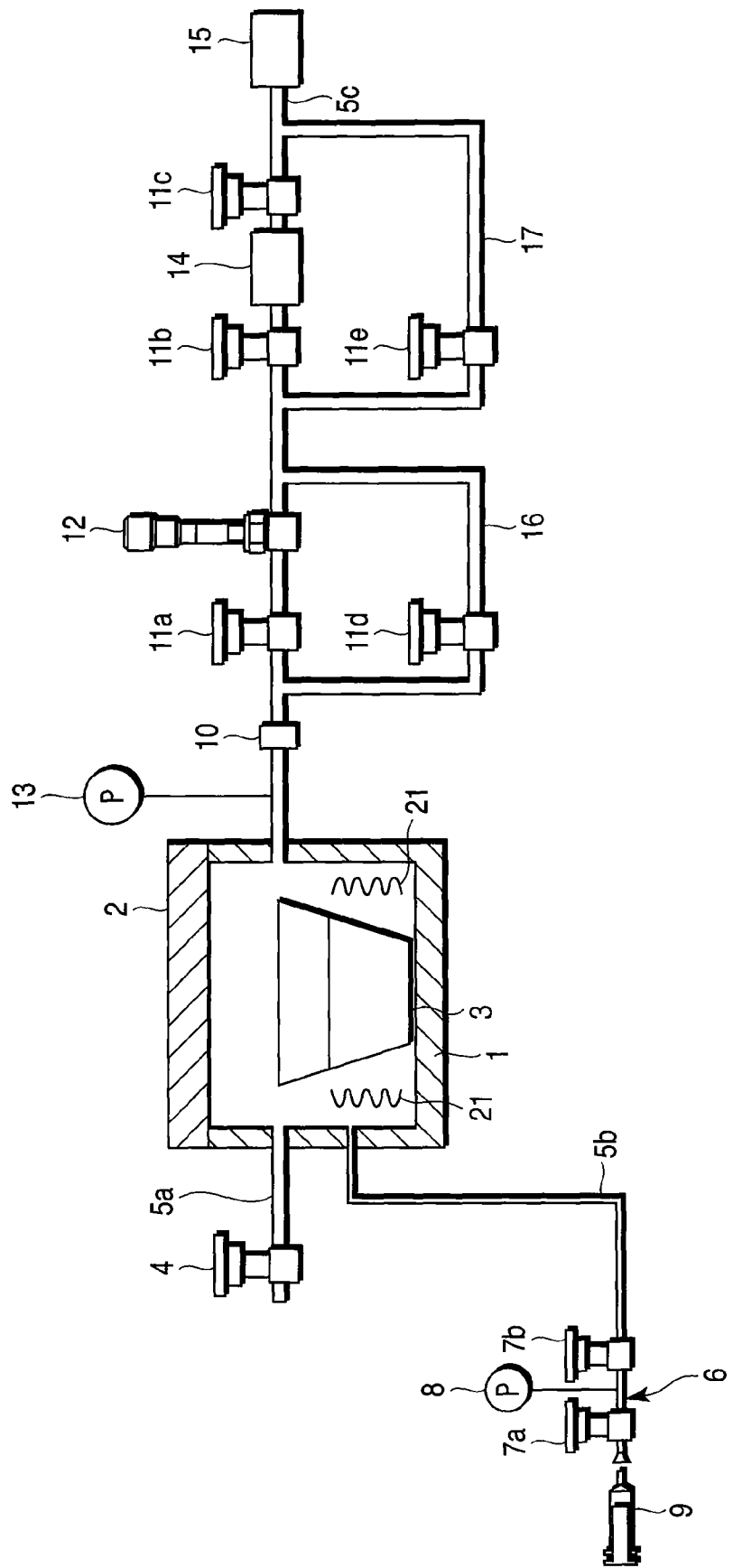
F I G. 4

GAS AMOUNT MEASUREMENT DEVICE

CROSS-REFERENCE TO RELATED APPLICATIONS

This application is based upon and claims the benefit of priority from prior Japanese Patent Application No. 2008-006205, filed Jan. 15, 2008, the entire contents of which are incorporated herein by reference.

BACKGROUND OF THE INVENTION

1. Field of the Invention

The present invention relates to a gas amount measurement device. More specifically, the present invention relates to a gas amount measurement device for measuring an entire amount of gas contained in molten metal or an amount of gas attached to an inclusion.

2. Description of the Related Art

Conventionally, a specific metal or alloy is used for a component such as a vehicle engine. Meanwhile, it is generally known that an amount of impurity gas per unit weight after refining a component is smaller than that before refining. This is because the impurity gas contained in a sample, that is, the component vaporizes during refining. In such a case, the refined component is molten again so as to reduce the amount of impurity gas in the component as much as possible. However, the melting of the refined component again undesirably causes a cost hike.

Furthermore, recycling has recently become popular for used metal products from the viewpoint of effective use of resources. However, if an aluminum product, for example, is melted, various types of gases such as hydrogen gas, carbon dioxide gas, oxygen gas, and nitrogen gas are released. Due to this, if the used aluminum product is cast in a mold, bubbles disadvantageously remain in an obtained product and pinholes or the like undesirably occur in the obtained product.

To solve these problems, it is proposed to measure a gas amount in molten metal. A measurement device including a chamber containing the molten metal, a pump setting an internal pressure of the chamber to a predetermined pressure, and a measuring unit measuring the internal pressure of the chamber, and measuring a gas amount from a pressure rise due to gas released from the molten metal is disclosed in, for example, Jpn. Pat. Appln. KOKAI Publication No. 2003-83865.

However, with the technique disclosed in Jpn. Pat. Appln. KOKAI Publication No. 2003-83865, the measurement device can only measure the total amount of all the gases present, but not individual gases.

BRIEF SUMMARY OF THE INVENTION

It is an object of the present invention to provide a gas amount measurement device capable of measuring an absolute amount of a specific type of gas contained in molten metal or attached to an inclusion and more accurately grasping characteristics of an obtained product.

According to an aspect of the present invention, there is a gas amount measuring device for measuring an amount of gas contained in molten metal or an amount of gas attached to an inclusion, comprising: a vacuum container containing therein the molten metal; a first pipe connected to the vacuum container, an air release valve being attached to the first pipe; a second pipe connected to the vacuum container, a calibration gas generator being attached to the first pipe; a third pipe connected to the vacuum container, a vacuum gauge, a first valve, a leak valve, a second valve, a turbomolecular pump, a third valve, and a roughing pump being attached to the third pipe in order from a vacuum container side; a first bypass pipe connecting the third pipe between the vacuum container and the first valve to the third pipe between the leak valve and the second valve, a fourth valve being attached to the first bypass pipe; and a second bypass pipe connecting the third pipe between the leak valve and the second valve to the third pipe between the third valve and the roughing pump, a fifth valve being attached to the second bypass pipe.

The present invention can provide a gas amount measurement device capable of measuring an absolute amount of a specific type of a gas contained in molten metal or attached to an inclusion and more accurately grasping characteristics of an obtained product.

BRIEF DESCRIPTION OF THE SEVERAL VIEWS OF THE DRAWINGS

FIG. 4 is an overall view of a gas amount measurement device according to a second embodiment of the present invention.

DETAILED DESCRIPTION OF THE INVENTION

Examples of a configuration of the calibration gas generator include a configuration of including two calibration valves arranged on a second pipe to be away from each other and a vacuum gauge measuring a pressure of a standard reference gas contained in the second pipe (pipe portion) between these calibration valves. A standard reference gas is fed to the pipe portion by, for example, a cylinder to maintain the internal pressure of the pipe portion at a certain air pressure. Therefore, if a temperature of the pipe portion is obtained while keeping a volume of the pipe portion at a certain volume and the internal pressure thereof at an air pressure of 1 atm, the number of moles of the standard reference gas of the pipe portion can be calculated from a general equation of pressure and volume, to be described later.

Specifically, the number of moles can be calculated by the following equation.

$$PV = nRT$$

In the equation, P denotes pressure (atmospheric pressure), V denotes the volume of the pipe portion (volume between the calibration valves) (liters), T denotes an absolute temperature of gas (K), R denotes a gas constant (constant value), and n denotes the number of moles of the standard reference gas.

According to the present invention, it is preferable to provide a heater in a vacuum container so as to heat a molten metal. Specifically, the heater is arranged outside of a sample cup as shown in FIG. 4. By doing so, it is possible to suppress a temperature fall of the molten metal contained in the sample cup.

According to the present invention, in order to calculate an absolute amount of a specific type of gas contained in the molten metal, the following process is carried out. First, a characteristic chart having constant pressure is obtained from the relationship between the internal pressure of the vacuum container and the time if the molten metal is absent in the vacuum container. Next, the molten metal is placed in the vacuum container, and an impurity gas amount Ss of impurity gas from the vacuum container in this state is detected based on the characteristic chart. The standard reference gas to be measured flows from a calibration gas generator into the vacuum container, and a standard reference gas amount Sr in this state is detected based on the characteristic chart and the impurity gas amount Ss, thereby obtaining the absolute amount of the gas amount of the specific type of gas.

DESCRIPTION OF THE PREFERRED EMBODIMENT EXAMPLE

A gas amount measurement device according to the present invention will be described hereinafter with reference to the accompanying drawings.

First Embodiment

Figure 1:
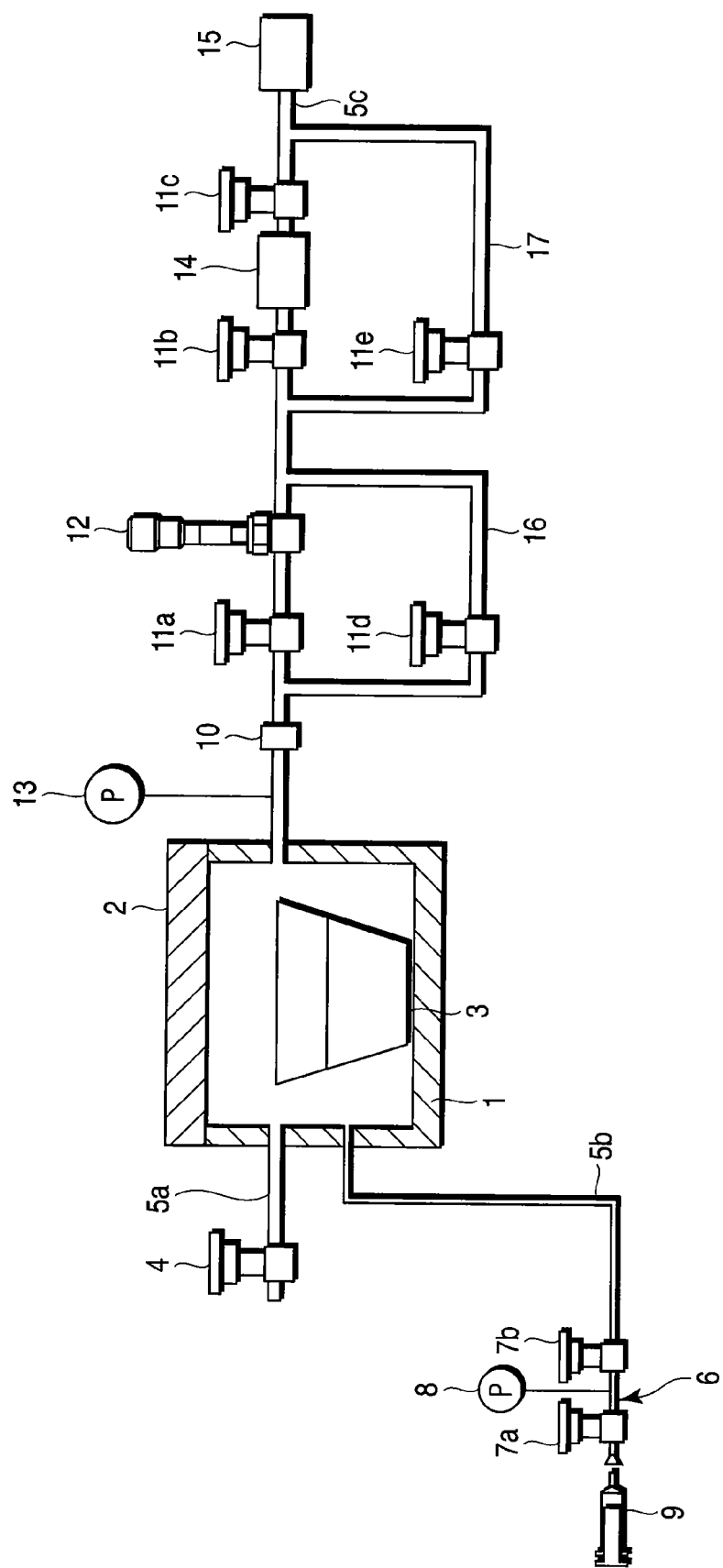
FIG. 1 is an overall view of a gas amount measurement device according to a first embodiment of the present invention.

Referring to FIG. 1, reference symbol 1 denotes a vacuum container including a freely opening/closing cover 2. A sample cup 3 containing therein molten metal (not shown) serving as a sample is arranged in the vacuum container 1. A first pipe 5a, to which an air release valve 4 is attached, is connected to an upstream side of the vacuum container 1. A second pipe 5b, to which a calibration gas generator 6 is attached, is connected to the upstream side of the vacuum container 1. The calibration gas generator 6 is configured to include calibration valves 7a and 7b, a manometer 8 connected to the pipe 5b between the valves 7a and 7b, and a cylinder 9. The internal pressure of the pipe 5b (pipe portion) between the valves 7a and 7b of the calibration gas generator 6 is regulated to an air pressure of 1 atm at the time of flowing the calibration gas.

A third pipe 5c is connected to a downstream side of the vacuum container 1. A vacuum gauge 13 measuring the internal pressure of the vacuum container 1, a filter 10, a first valve 11a, a leak valve 12, a second valve 11b, a turbomolecular pump 14, a third valve 11c, and a roughing pump 15 are arranged on the third pipe 5c in order from vacuum container 1 side. The second valve 11b and the third valve 11c are provided to prevent the turbomolecular pump 14 from being destroyed when the sample is put into or taken from the vacuum container 1. The turbomolecular pump 14, which is used when an amount of gas released from the molten metal is small, constantly operates. This is intended to prevent working time loss by turning on or off the turbomolecular pump 14.

The pipe 5c between the filter 10 and the first valve 11a is connected to the pipe 5c between the leak valve 12 and the second valve 11b by a first bypass pipe 16. A fourth valve 11d is provided on the first bypass pipe 16. The pipe 5c between the leak valve 12 and the second valve 11b is connected to the pipe 5c between the third valve 11c and the roughing pump 15 by a second bypass pipe 17. A fifth valve 11e is provided on the second bypass pipe 17. The bypass pipes 16 and 17 are used if an amount of the released gas is large and the roughing pump 15 directly evacuates the gas.

The operation performed by the gas amount measurement device configured as stated above is as follows.

(1) Before the Molten Metal is Contained in the Sample Cup 3:

First, the first valve 11a, the second valve 11b, and the fourth valve 11d are fully closed, the third valve 11c and the fifth valve 11e are fully opened, and the roughing pump 15 is operated. Thereafter, the turbomolecular pump 14 is operated. In this state, the air release valve 4 is fully opened and the cover 2 of the vacuum container 1 is lifted. The sample cup 3 is put into the vacuum container 1 and the cover 2 is closed. The air release valve 4 and the third valve 11c are fully closed, the fourth valve 11d is fully opened, and the gas within the vacuum container 1 is evacuated by the roughing pump 15 through the first and second bypass pipes 16 and 17. If the amount of the gas within the vacuum container 1 is small, then the fifth valve 11e is fully closed with the fourth valve 11d kept fully opened, the second valve 11b and the third valve 11c are fully opened, and the gas within the vacuum container 1 is evacuated by the turbomolecular pump 14 and the roughing pump 15 only through the first bypass pipe 16. By measuring the internal pressure of the vacuum container 1 using the vacuum gauge 13 in this state, a graph having gradually falling pressure is obtained as indicated by a curve A shown in FIG. 2.

(2) After the Molten Metal is Placed in the Sample Cup 3:

First, the roughing pump 15 is stopped (the roughing pump 15 is stopped after the turbomolecular pump 14 is stopped if the turbomolecular pump 14 operates), and then the air release valve 4 is released (returned to an air pressure of 1 atm). After the cover 2 of the vacuum container 1 is lifted and the sample is put into the sample cup 3, the cover 2 is closed. Next, by performing a similar operation to that described in (1) above, the internal pressure of the vacuum container 1 is measured using the vacuum gauge 13. As a result, a graph having large and small peaks is obtained as indicated by a curve B shown in FIG. 2.

Figure 2:
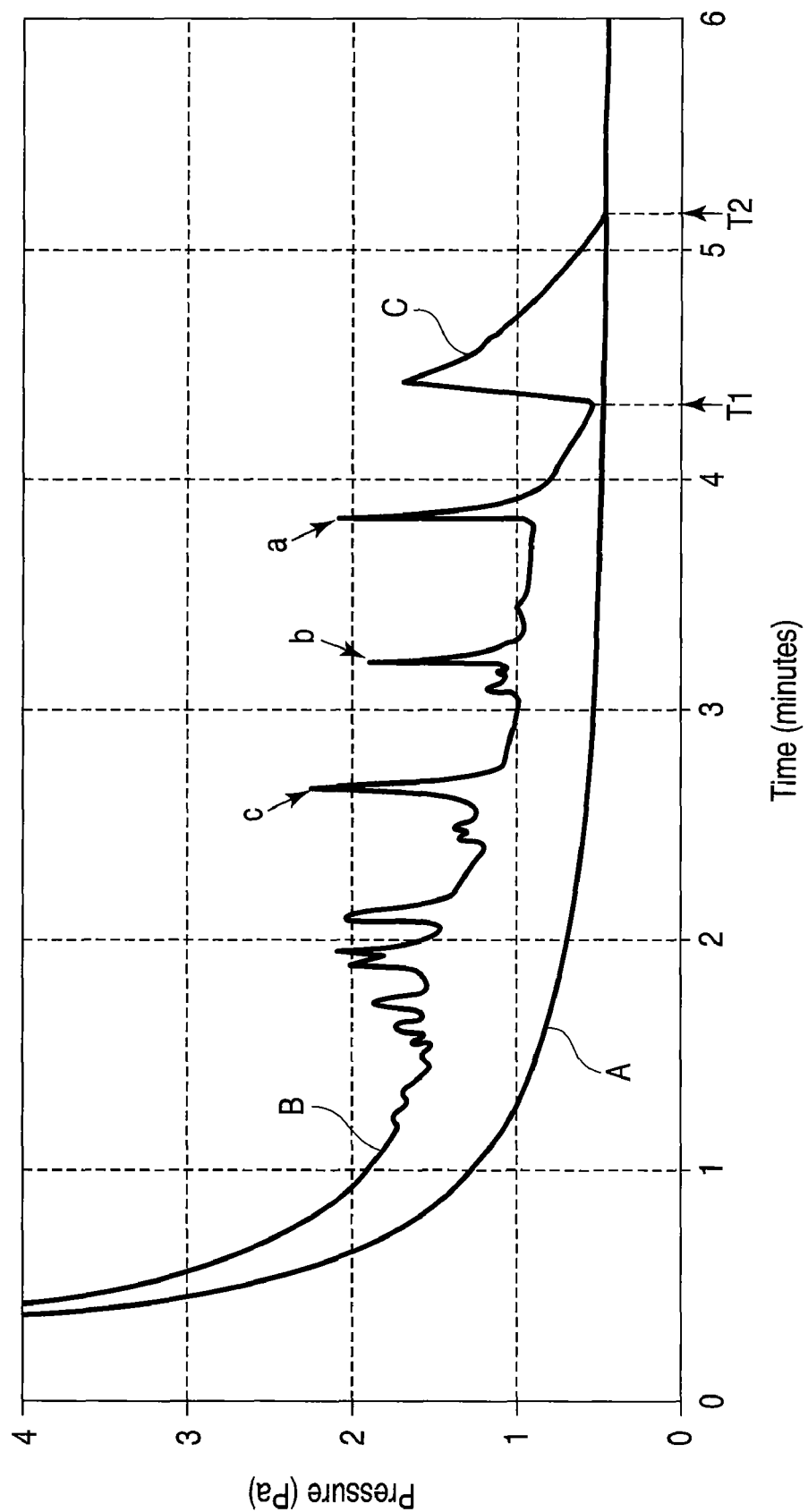
FIG. 2 is a characteristic chart showing the relationship between an internal pressure of a vacuum container and time whether a sample is present (curve B) or absent (curve A) in the gas amount measuring device shown in FIG. 1.

(3) Supply of Calibration Gas:

After passage of time $T_1$ (e.g., four minutes and 20 seconds) since the sample is put into the sample cup 3 within the vacuum container 1, a standard reference gas at an air pressure of 1 atom, e.g., $N_2$ is input into the pipe 5b (pipe portion) between the calibration valves 7a and 7b. The calibration valve 7b is opened to introduce $N_2$ into the vacuum container 1 from the pipe 5b for predetermined time $(T_2-T_1)$. As a result, a curve C having a longer tailed large peak caused by the calibration gas is obtained as indicated by a curve C shown in FIG. 2. Using the curves C and A, the number of molecules Sr from $T_2$ to $T_1$ is obtained. Since PV=nRT (where P denotes a pressure of the pipe portion, V denotes a volume of the pipe portion, n denotes the number of moles, R denotes a constant, and T denotes a temperature of the pipe portion), the number of moles n can be obtained. FIG. 2 shows that (1) the gas is released to the space of the vacuum container 1 from within the molten metal contained in the sample cup 3 and that (2) released conditions of the gas is composite simultaneous gas release with appearance of large and small pressure peaks and static gas release without appearance of pressure peaks.

Figure 3:
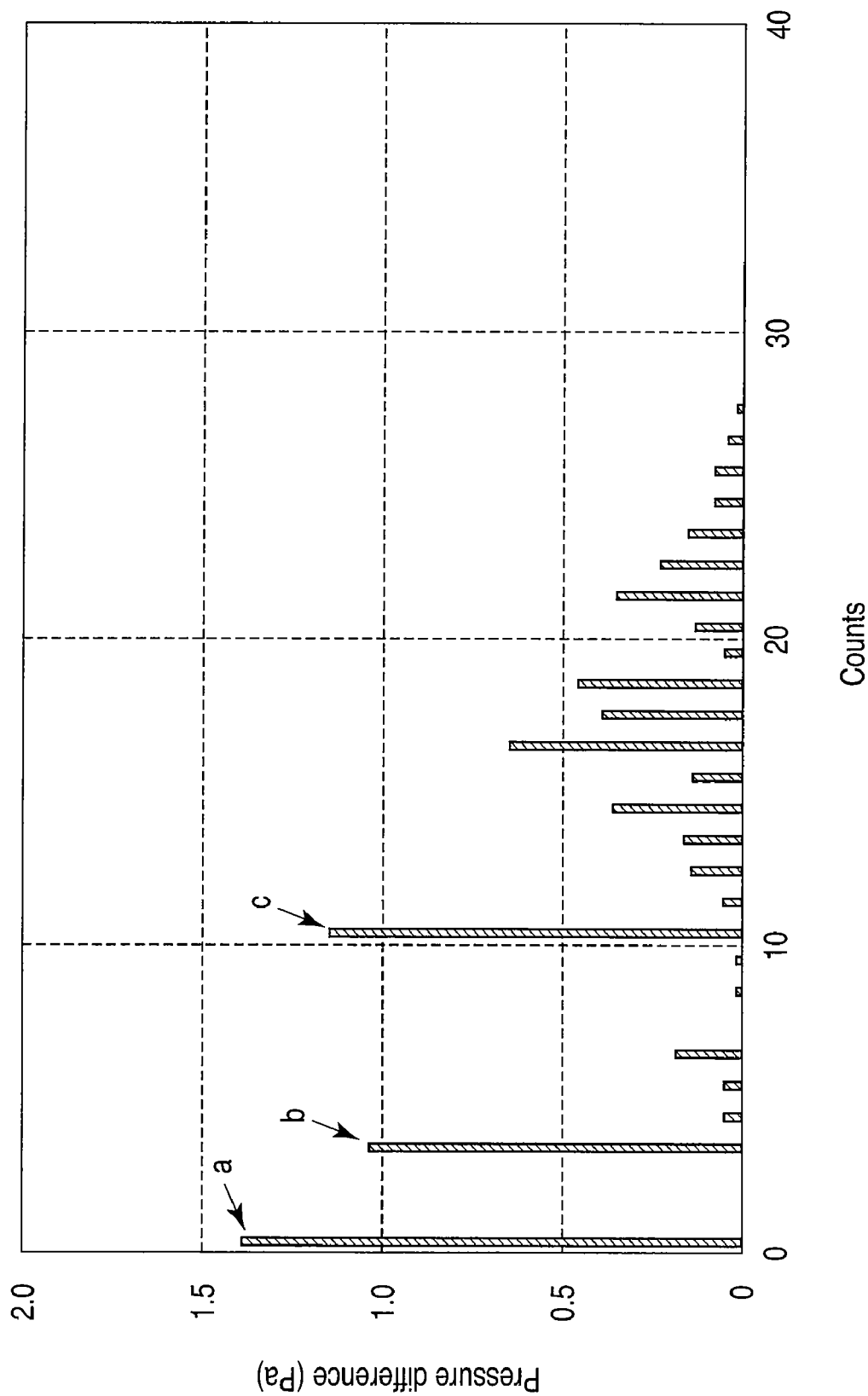
FIG. 3 is a characteristic chart showing the relationship between a pressure difference corresponding to the characteristic chart of FIG. 2 and the counts of the same peak pressures in FIG. 2.

FIG. 3 is a characteristic chart showing the relationship between pressure difference corresponding to the characteristic chart of FIG. 2 and the counts of the same peak pressures in FIG. 2. FIG. 3 shows a projecting gas released amount in pressure per peak event as a function of the peak counts from the molten metal. The projecting gas released amount is proportional to the peak pressure. In this case, as the peak pressure is higher and the peak counts is larger, a large amount of gas that tends to form gas bubbles (bubbles) is contained in the molten metal.

In this way, the gas amount measurement device according to the first embodiment is configured to include the calibration gas generator 6 that is provided on the upstream side of the vacuum container 1 and that includes the calibration valves 7a and 7b, the manometer 8 connected to the pipe portion between the valves 7a and 7b, and the cylinder 9. It is, therefore, possible to measure the amount of each type of gas.

In the first embodiment, the instance of using $N_2$ as the standard reference gas has been described. However, the present invention is not limited to the instance and an arbitrary type of gas such as $H_2$ or He can be used as the standard reference gas.

Second Embodiment

Referring to FIG. 4, a gas amount measurement device according to a second embodiment will be described. The same constituent elements shown in FIG. 4 as those shown in FIG. 1 are denoted by the same reference symbols and will not be described herein. The second embodiment is characterized, as compared with the first embodiment shown in FIG. 1, in that a heater 21 is provided around the sampling cup 3.

According to the second embodiment, temperature fall of the molten metal contained in the sample cup 3 can be suppressed by presence of the heater 21.

The present invention is not limited to the first and second embodiments but can be carried out by modifying the constituent elements within the scope of the invention. Furthermore, various inventions can be created by appropriate combinations of a plurality of constituent elements disclosed in the first and second embodiments. For example, several constituent elements can be eliminated from all the constituent elements shown in the first and second embodiments. Specifically, while the filter is provided on the pipe, the filter is not always necessary. In addition, the heater arranged around the sampling cup is not always necessary. Further, the constituent elements of the first and second embodiments can be appropriately combined. Further, while the instance of measuring the amount of pure gas contained in the molten metal has been described in the first and second embodiments, the present invention is also applicable to an instance of observing an inclusion while measuring the amount of gas attached to the inclusion.

What is claimed is:

1. A gas amount measuring device for measuring an amount of gas contained in molten metal or an amount of gas attached to an inclusion, comprising:
a vacuum container containing therein the molten metal;
a first pipe connected to the vacuum container, an air release valve being attached to the first pipe;
a second pipe connected to the vacuum container, a calibration gas generator being attached to the first pipe;
a third pipe connected to the vacuum container, a vacuum gauge, a first valve, a leak valve, a second valve, a turbomolecular pump, a third valve, and a roughing pump being attached to the third pipe in order from a vacuum container side;
a first bypass pipe connecting the third pipe between the vacuum container and the first valve to the third pipe between the leak valve and the second valve, a fourth valve being attached to the first bypass pipe; and
a second bypass pipe connecting the third pipe between the leak valve and the second valve to the third pipe between the third valve and the roughing pump, a fifth valve being attached to the second bypass pipe.

2. The gas amount measuring device according to claim 1, wherein a heater heating the molten metal is provided in the vacuum container.

3. The gas amount measuring device according to claim 1, wherein the calibration gas generator includes
two calibration valves arranged on the second pipe to be away from each other; and
a pressure gauge measuring a pressure of a standard reference gas contained in a pipe portion between the two calibration valves.

4. The gas amount measuring device according to claim 3, wherein a heater heating the molten metal is provided in the vacuum container.

5. The gas amount measuring device according to any one of claims 1 to 4,
wherein an absolute amount of a standard reference gas is calculated by obtaining a characteristic chart showing constant pressure from a relationship between an internal pressure of the vacuum container and time if the molten metal is not present in the vacuum container, detecting an impurity gas amount Ss from the vacuum container in a state of containing the molten metal in the vacuum container based on the characteristic chart, and detecting a standard reference gas amount Sr in a state of flowing the standard reference gas to be measured from the calibration gas generator into the vacuum container based on the characteristic chart and the impurity gas amount Ss.

* * * * *